United States Patent [19]

Keister

[11] Patent Number: 5,215,978
[45] Date of Patent: Jun. 1, 1993

[54] METHOD OF ENHANCING EGG LAYING IN TURKEYS USING EPOSTANE

[75] Inventor: Don M. Keister, Grayson, Ga.

[73] Assignee: The Upjohn Company, Kalamazoo, Mich.

[21] Appl. No.: 778,206

[22] PCT Filed: May 31, 1990

[86] PCT No.: PCT/US90/02933

§ 371 Date: Dec. 13, 1991

§ 102(e) Date: Dec. 13, 1991

Related U.S. Application Data

[63] Continuation of Ser. No. 367,420, Jun. 16, 1989, abandoned.

[51] Int. Cl.$^5$ .............................................. A61K 31/58
[52] U.S. Cl. ...................................................... 514/172
[58] Field of Search ........................................... 514/172

[56] References Cited

U.S. PATENT DOCUMENTS 4,160,027 7/1979 Christiansen ........................ 514/172

FOREIGN PATENT DOCUMENTS 0253099 1/1988 European Pat. Off. .
0256224 2/1988 European Pat. Off. .
0361239 4/1990 European Pat. Off. .

OTHER PUBLICATIONS

J. Reprod. Fert., vol. 79, No. 1, (1987) Journals of Reproduction & Fertility Ltd., R. Webb: "Increasing Ovulation Rate and Lambing Rate in Sheep by Treatment With a Steroid Enzyme Inhibitor", pp. 231–240.

Fertility and Sterility, vol. 42, No. 6, Dec. 1984, (US), N. S. Pattison et al.: "Inhibition of 3-Hydroxysteroid Dehydrogenase (3β-HSD) Activity in First- and Second-Trimester Human Pregnancy and the Luteal Phase using Epostane", pp. 875–881.

Sterling Drug Inc. Presentation to Financial Community Oct. 23, 1986.

*Primary Examiner*—Frederick E. Waddell
*Assistant Examiner*—K. Weddington
*Attorney, Agent, or Firm*—Gregory W. Steele

[57] ABSTRACT

The method of enhancing egg laying in the turkey which comprises administering to a turkey hen an amount of epostane sufficient to increase significantly the number of eggs laid during the egg laying cycle of said turkey hen is disclosed.

5 Claims, No Drawings

METHOD OF ENHANCING EGG LAYING IN TURKEYS USING EPOSTANE

CROSS-REFERENCE TO RELATED APPLICATIONS

This application is the national phase of international application PCT/US90/02933, filed 31 May, 1990, which is a continuation of U.S. Ser. No. 367,420, filed 16 Jun. 1989, now abandoned.

BACKGROUND OF THE INVENTION

1. Field of the Invention

The invention relates to a process of enhancing egg laying in turkeys using epostane.

2. Information Disclosure Statement

Epostane is the United States Adopted Name (1988 USAN and the USP Dictionary of Drug Names, 1961-1987 Cumulative List) for $(4\alpha, 5\alpha, 17\beta)$-4,5-epoxy-3,17-dihydroxy-4,17-dimethylandrost-2-ene-2-carbonitrile having the structural formula

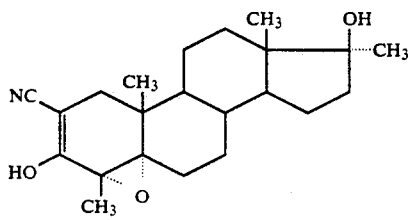

Formula I (representing the enol form) and having utility as an interceptive (pregnancy disrupting) agent.

Christiansen U.S. Pat. No. 4,160,027 issued Jul. 3, 1979 describes epostane as the product of part (f) of EXAMPLE 1, that is, $4\alpha, 5\beta$-epoxy-17$\beta$-hydroxy-4,17-dimethyl-3-oxoandrostane-2$\alpha$-carbonitrile having the structural formula

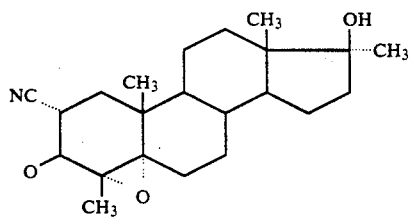

Formula II which represents the keto form of epostane. The patent shows the interceptive utility of epostane in the rat and the monkey.

Epostane has been studied for effects on fertility in numerous mammalian species and the published results of the studies constitute a bibliography which in March of 1989 numbered 66 references, none of which relates to any avian species.

Three of the references for which the bibliography contains abstracts relate to ovulation. De Paolo (J. Endocrinol., vol. 118(1), pp. 59-68, 1988) and Snyder et al. (Proc. Soc. Exp. Biol. Med., vol 176(3), pp. 238-242, 1984) show inhibition of ovulation in the rat with epostane and Webb (J. Reprod. Fertil., vol 79(1), pp. 231-240, 1987) shows increase in ovulation rate in the ewe with epostane.

The only prior art known to applicant relating to use of epostane in an avian species are as follows: (i) an unpublished report showing dose related decrease of plasma progesterone and estradiol concentrations in the chicken therewith. The report is in the form of a letter dated Aug. 19, 1985 from Peter J. Sharp of The Agricultural and Food Research Council Poultry Research Centre at Midlothian, Scotland, to H. Loison of Sterling Winthrop Group Ltd. in Guildford, England, through whom espostane for the work had been supplied; (ii) a publication entitled STERLING DRUG INC. PRESENTATION TO FINANCIAL COMMUNITY dated Oct. 23, 1986 in a part entitled EPOSTANE at pages 79-80 states at page 80 that "[t]he endocrine effects [of epostane] on egg production in poultry are also being pursued" and that "[t]his latter indication is of particular importance in the broiler industry". The first statement merely sets forth a goal and does not identify a species. The second statement identifies the chicken as a species "of particular importance" and does not mention the turkey. Accordingly the presently described invention is not described or made obvious by the publication. Moreover, as shown below epostane was found not effective in enhancing egg laying in the chicken.

Broodiness in the turkey hen is a physiological condition characterized by aggressive territorial nest protection and increase nesting behavior with cessation of egg production, which together with costs of additional labor and facilities needed to maintain broody hens result in significant economic loss in the turkey industry. The presently described and claimed invention fills a need for a solution to the egg production aspect of the problem in the turkey industry.

SUMMARY OF THE INVENTION

The invention is the method of enhancing egg laying in the turkey which comprises administering to a turkey hen an amount of epostane sufficient to increase significantly the number of eggs laid during the egg laying cycle of said turkey hen.

DETAILED DESCRIPTION OF THE INVENTION INCLUSIVE OF THE PREFERRED EMBODIMENTS

The egg laying cycle in the turkey hen is about six months in duration. Near the end of the cycle egg production declines. At the end of the cycle the hen molts. Egg production ceases and rises again as the new cycle ensues. A hen normally produces 75-90 eggs per cycle, thus one egg every 2.0-2.4 days. As stated above broodiness is also an important factor effecting egg production in turkey hens. Accordingly in carrying out the invention effects of epostane on factors which relate to broodiness and egg productivity as well as egg production itself were also studied.

Any amount of epostane sufficient to effect a significant increase in the number of eggs laid during the egg laying cycle can be used. The preferred dose is in the range of 0.1-10 mg./kg. per day. The epostane can be prepared for administration in any pharmaceutically acceptable oral or parenteral dosage form. The oral dosage form can be solid or liquid and thus granules, capsule, tablet, solution, suspension or emulsion. The parenteral dosage form can be solution, suspension or emulsion. An ethanol-cottonseed oil vehicle is preferred. An oral dosage form is preferred. Gelatin capsules can be used, but the preferred oral dosage form is granules which may be mixed into or top-dressed onto the feed. Sustained release dosage forms can be used. The daily dose can be given for as few as one day or as many as all the days of the egg laying cycle. Daily doses for one day and five weeks (weeks 3-7) of the cycle were used in the tests described below.

In a first test of the invention the effects of a single 0, 1.25, 2.5, 5 or 10 mg./kg. oral or parenteral dose of epostane on blood plasma concentration of progesterone, estradiol, corticosterone and prolactin and on egg production in the turkey hen were determined. One hundred hen (110) 52-week old first cycle turkey hens were divided randomly into 10 groups of 11 hens each for the test. The oral doses of epostane were given in gelatin capsules. For parenteral administration the epostane was dissolved in ethanol-cottonseed oil (10:90) at a concentration of 20 mg./ml. and given subcutaneously. Blood samples were taken one week before medication and at 6, 12, 24 and 48 hours postmedication. Analysis of the four blood plasma variables was done by radioimmunoassay. Egg production was measured for 12 days before medication and 3 days postmedication, whereupon the hens were sacrificed. Data were analyzed by analysis of variance.

Unlike the effect of epostane on blood plasma progesterone concentration in mammals no significant overall effect of dose or route of administration of epostane on this variable was observed in the turkey hen. A significant ($p \leq 0.0001$) decrease therein was correlated with sampling time at 6 and 12 hours postmedication, but this was overcome by rebound at 24 and 48 postmedication so that no significant overall effect of sampling time was shown. Significant reduction of estradiol concentration based overall on dose of epostane ($p \leq 0.0001$) and sampling time ($p \leq 0.02$) was observed, but the effect of route of administration was not significant. Significant reduction of corticosterone concentration based overall on dose ($p \leq 0.0001$) and route of administration ($p \leq 0.02$) of epostane and sampling time ($p \leq 0.03$) was observed. No significant overall effect of does or route of administration of epostane or sampling time on prolactin concentration was observed.

Egg production was measured as percent hen-day egg production, which is defined for a given group of hens and a given number of days as:

percent hen-day egg production = the number of eggs laid × 100/the number of hens × the number of days Egg production results of the first test are presented in Table I.

TABLE I

| | First Test - Egg Production | | | |
|---|---|---|---|---|
| Epostane Dose (mg./kg.) | Percent Hen-Day Egg Production | | | |
| | Premedication | | Postmedication | |
| | Oral | Parenteral | Oral | Parenteral |
| 0 | 47.0 | 34.5 | 24.0 | 51.7 |
| 1.25 | 37.3 | 35.5$^a$ | 26.7 | 60.0$^a$ |
| 2.50 | 27.1 | 30.9 | 12.0 | 46.7 |
| 5.00 | 29.8 | 30.9$^b$ | 21.0 | 70.0$^b$ |
| 10.00 | 57.3 | 39.1 | 66.7 | 56.7 |

$^{a,b}$Significantly different ($p \leq 0.03$)

As shown by Table I the 1.25 and 5.00 mg./kg. parenteral dose groups showed significant increased in egg production. This was considered encouraging because only a single dose was given to each hen and only three days' egg production postmedication was measured.

In a second test of the invention the effects of 0, 0.313, 0.625, 1.25 and 2.50 mg./kg. oral doses of epostane daily for five weeks on blood plasma concentration of progesterone, estradiol, corticosterone, prolactin, calcium and protein, egg production and egg characteristics in the broody-prone turkey hen were determined. Two hundred (200) first cycle turkey hens prone to broodiness were divided randomly into 5 groups of 40 hens each and induced to molt and thereby to begin their second laying cycles synchronously. The daily oral doses of epostane were given in gelatin capsules beginning with the third week of the egg laying cycle. Blood samples were taken daily from 10 hens in each dose daily. Egg production and nesting behavior were determined six times daily. The hens were sacrificed two weeks after termination of medication and at necropsy the ovaries and uterus were examined. Analysis of progesterone, estradiol, corticosterone and prolactin concentrations were done by radiommunoassay. Analysis of calcium and protein concentrations was colorimetrically. Data were analyzed by analysis of variance except egg characteristics and necropsy data, which were analyzed by chi square analysis.

At necropsy the ovary of each hen which completed the test was examined. A normal ovary was considered indicative of egg productivity during the test period. A tumorous, juvenile or regressed ovary or one having atresic follicles was considered indicative of lack of egg productivity during the test period. The number of hens having normal ovaries (11/37, 10/38, 19/27, 13/40) was significantly greater ($p \leq 0.27$) in the groups medicated with epostane (0.313, 0.625, 1.25, 2.50 mg./kg. respectively) than in the unmedicated group (7/40). Each ovary was also examined for loss of hierarchy of follicles and number of primary follicles. The number of hens showing loss of hierarchy of follicles (5/35, 9/38, 7/36, 8/40) was significantly greater ($p \leq 0.034$) in the groups medicated with epostane (0.313, 0.625, 1.25 mg./kg. respectively) than in the unmedicated group (none). The number of primary follicles was significantly greater ($p \leq 0.028$) in the groups medicated with epostane than in the unmedicated group. Epostane therefore significantly reversed the tendency toward atresic ovaries and the consequent inability to produce eggs and significantly increase recruitment of follicles for ovulation and the consequent ability to produce more eggs in turkey hens prone to broodiness.

Overall effects of epostane medication on blood plasma parameters are shown in Table II.

TABLE II

| Second Test - Overall Blood Plasma Parameter Effects | | |
|---|---|---|
| | Concentration | |
| Parameter (Concentration Units) | Unmedicated Hens | Epostane Medicated Hens |
| Progesterone (pg./ml.) | 561$^a$ | 825$^a$ |
| Estradiol (pg./ml.) | 57.66$^b$ | 61.14$^b$ |
| Corticosterone (ng./ml.) | 3.93$^c$ | 5.07$^c$ |
| Prolactin (ng./ml.) | 1049 | 1095 |
| Calcium (mg./dl.) | 15.8 | 16.1 |
| Protein (g./dl.) | 4.98 | 5.02 |

$^a$Significantly different ($p \leq 0.006$)
$^b$Significantly different ($p \leq 0.01$)
$^c$Significantly different ($p \leq 0.005$)

Increases in progesterone, estradiol and corticosterone concentrations were even more significantly ($p \leq 0.0001$) increased in productive hens than in non-productive hens. Plasma protein concentrations were also significantly ($p \leq 0.0001$) increased in productive hens. Plasma prolactin concentrations were significantly ($p \leq 0.0001$) described in productive hens.

Egg production results of the second test are shown in Table III.

TABLE III

| | Second Test - Egg Production | | | | |
|---|---|---|---|---|---|
| | Percent Hen-Day Egg Production Epostane Dose (mg./kg.) | | | | |
| Week | 0 | 0.313 | 0.625 | 1.25 | 2.50 |
| 1 | 40 | 33 | 25 | 42 | 34 |
| 2 | 31 | 25 | 19 | 28 | 28 |
| 3 | 22 | 12 | 19 | 20 | 20 |
| 4 | 19 | 4 | 11 | 16 | 18 |
| 5 | 14 | 7 | 8 | 22 | 23 |
| 6 | 12 | 15 | 11 | 32 | 25 |
| 7 | 12 | 9 | 15 | 30 | 21 |
| 8 | 4 | 5 | 12 | 19 | 11 |
| 9 | 4 | 4 | 11 | 7 | 9 |

Egg production declined steadily in the unmedicated group due to increase broodiness during the test period. Epostane appeared to reverse this tendency partially in the medicated groups. During week 5 (the third week of medication) egg production was significantly greater ($p \leq 0.04$) in the 1.25 and 2.50 mg./kg. dose groups than in the 0.313 and 0.625 mg./kg. dose groups. During weeks 6 and 7 (the fourth and fifth weeks of medication) egg production was significantly greater ($p \leq 0.04$ and 0.01, respectively) in the 1.25 and 2.50 mg./kg. dose groups than in the 0, 0.313 and 0.625 mg./kg. dose groups. During week 8 (the first week postmedication) egg production was significantly greater ($p \leq 0.008$) in the 1.25 mg./kg. dose group than in the 0 and 0.313 mg./kg. dose groups. This pattern of significance is not greatly affected by correcting the results for hens which were unproductive or which died or by normalizing the medicated groups against the unmedicated group.

Egg weights and eggshell weights were slightly decreased in the medicated dose groups, but the specific gravity of the eggs was not affected by medication. These effects are not considered important.

COMPARATIVE TEST IN THE CHICKEN

A test was conducted to determine the effects of epostane on blood plasma hormone concentrations and egg laying efficiency in chickens nearing the termination of their active egg production. Two hundred (200) hens were divided into 10 groups of 20 hens each for the test. In duplicate groups epostane was given in the feed daily for four weeks at 0, 1.25, 2.5, 5.0 and 10 mg./kg. Blood plasma concentrations of progesterone, estradiol, corticosterone and prolactin were determined in one of the duplicate sets of groups. Egg production and egg quality were determined in all groups. Preliminary evaluation of the data shows that epostane did not have a major effect on blood plasma hormone concentrations or egg laying efficiency in the chicken.

I claim:

1. The method of enhancing egg laying in the turkey which comprises administering to a turkey hen an amount of epostane sufficient to increase significantly the number of eggs laid during the egg laying cycle of said turkey hen.

2. The method according to claim 1 wherein the amount of epostane is in the range of 0.01-10 mg./kg. per day.

3. The method according to claim 2 wherein the daily dose is given for as few as one day or as many as all the days of the egg laying cycle.

4. The method according to claim 3 wherein the epostane is administered orally.

5. The method according to claim 3 wherein the epostane is administered parenterally.

* * * * *